US009994720B2

(12) United States Patent
Dacko et al.

(10) Patent No.: US 9,994,720 B2
(45) Date of Patent: Jun. 12, 2018

(54) METHODS FOR PRODUCING 1,5,7-TRIAZABICYCLO[4.4.0]DEC-5-ENE BY REACTION OF A DISUBSTITUTED CARBODIIMIDE AND DIPROPYLENE TRIAMINE

(71) Applicant: PPG Industries Ohio, Inc., Cleveland, OH (US)

(72) Inventors: Christopher Dacko, Pittsburgh, PA (US); Richard F. Karabin, Ruffs Dale, PA (US); Craig Wilson, Allison Park, PA (US); Steven R. Zawacky, Pittsburgh, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days. days.

(21) Appl. No.: 14/794,860

(22) Filed: Jul. 9, 2015

(65) Prior Publication Data
US 2015/0307722 A1 Oct. 29, 2015

Related U.S. Application Data

(62) Division of application No. 13/455,651, filed on Apr. 25, 2012, now Pat. No. 9,108,968.

(51) Int. Cl.
*C07D 487/04* (2006.01)
*C09D 163/00* (2006.01)
*C09D 5/44* (2006.01)

(52) U.S. Cl.
CPC .......... *C09D 5/443* (2013.01); *C07D 487/04* (2013.01); *C09D 163/00* (2013.01)

(58) Field of Classification Search
CPC ..................................... C09D 5/443
USPC .............................................. 544/279
See application file for complete search history.

(56) References Cited

U.S. PATENT DOCUMENTS

| 2,783,894 | A | 3/1957 | Lovell et al. |
| 2,915,475 | A | 12/1959 | Bugosh |
| 2,917,426 | A | 12/1959 | Bugosh |
| 3,025,233 | A | 3/1962 | Figert |
| 3,031,417 | A | 4/1962 | Bruce |
| 3,031,418 | A | 4/1962 | Bugosh |
| 3,056,747 | A | 10/1962 | Arthur, Jr. |
| 3,117,944 | A | 1/1964 | Harrell |
| 3,234,075 | A | 2/1966 | Braitberg |
| 3,242,073 | A | 3/1966 | Guebert et al. |
| 3,352,424 | A | 11/1967 | Guebert et al. |
| 3,408,315 | A | 10/1968 | Paine |
| 3,793,061 | A | 2/1974 | Hammel et al. |
| 3,852,202 | A | 12/1974 | Wells et al. |
| 3,947,562 | A | 3/1976 | Grimshaw et al. |
| 4,007,113 | A | 2/1977 | Ostreicher |
| 4,007,114 | A | 2/1977 | Ostreicher |
| 4,059,119 | A | 11/1977 | Grossman |
| 4,149,549 | A | 4/1979 | Grossman |
| 4,153,661 | A | 5/1979 | Ree et al. |
| 4,179,438 | A | 12/1979 | Haase et al. |
| 4,230,573 | A | 10/1980 | Kilty et al. |
| 4,242,226 | A | 12/1980 | Siren |
| 4,282,261 | A | 8/1981 | Greene |
| 4,288,462 | A | 9/1981 | Hou et al. |
| 4,305,782 | A | 12/1981 | Ostreicher et al. |
| 4,309,247 | A | 1/1982 | Hou et al. |
| 4,321,288 | A | 3/1982 | Ostreicher |
| 4,331,631 | A | 5/1982 | Chapman et al. |
| 4,366,068 | A | 12/1982 | Ostreicher et al. |
| 4,395,332 | A | 7/1983 | Klein |
| 4,433,697 | A | 2/1984 | Cline et al. |
| 4,455,187 | A | 6/1984 | von Blücher et al. |
| 4,473,474 | A | 9/1984 | Ostreicher et al. |
| 4,500,647 | A | 2/1985 | Solomon |
| 4,510,193 | A | 4/1985 | Blücher et al. |
| 4,511,473 | A | 4/1985 | Hou |
| 4,523,995 | A | 6/1985 | Pall et al. |
| 4,536,440 | A | 8/1985 | Berg |
| 4,555,347 | A | 11/1985 | O'Dowd et al. |
| 4,569,756 | A | 2/1986 | Klein |
| 4,604,208 | A | 8/1986 | Chu et al. |
| 4,606,823 | A | 8/1986 | Lucas, III |
| 4,617,182 | A | 10/1986 | Ostreicher |
| 4,664,683 | A | 5/1987 | Degen et al. |
| 4,673,504 | A | 6/1987 | Ostreicher et al. |
| 4,677,019 | A | 6/1987 | Von Blücher |
| 4,708,803 | A | 11/1987 | Ostreicher et al. |
| 4,711,793 | A | 12/1987 | Ostreicher et al. |
| 4,743,418 | A | 5/1988 | Barnes, Jr. et al. |
| 4,761,323 | A | 8/1988 | Mühlratzer et al. |
| 4,807,619 | A | 2/1989 | Dyrud et al. |
| 4,824,451 | A | 4/1989 | Vogt et al. |
| 5,085,784 | A | 2/1992 | Ostreicher |
| 5,104,546 | A | 4/1992 | Filson et al. |
| 5,109,311 | A | 4/1992 | Hanazono et al. |
| 5,126,044 | A | 6/1992 | Magnusson et al. |
| 5,147,722 | A | 9/1992 | Koslow |
| 5,189,092 | A | 2/1993 | Koslow |
| 5,219,577 | A | 6/1993 | Kossovsky et al. |
| 5,225,078 | A | 7/1993 | Polasky et al. |

(Continued)

FOREIGN PATENT DOCUMENTS

WO 2009021095 2/2009
WO 2011079041 6/2011

OTHER PUBLICATIONS

Shen, Hao et al., "Ti-amide Catalyzed Synthesis of Cyclic Guanidines from Di-Triamines and Carbodiimides", Organic Letters; Aug. 4, 2011; pp. 4562-4565, vol. 13, No. 17, American Chemical Society.

(Continued)

*Primary Examiner* — Susanna Moore
(74) *Attorney, Agent, or Firm* — Charles M. Yeomans

(57) ABSTRACT

Methods for producing 1,5,7-triazabicyclo[4.4.0]dec-5-ene using a disubstituted carbodiimide, dipropylene triamine and optionally an ethereal solvent and/or an alcohol are disclosed. Use of 1,5,7-triazabicyclo[4.4.0]dec-5-ene produced by this method in an electrodepositable coating composition, and electrophoretic deposition of such coating onto a substrate to form a coated substrate, are also disclosed.

13 Claims, No Drawings

(56) References Cited

U.S. PATENT DOCUMENTS

| | | |
|---|---|---|
| 5,307,796 A | 5/1994 | Kronzer et al. |
| 5,350,443 A | 9/1994 | von Blücher et al. |
| 5,366,636 A | 11/1994 | Marchin et al. |
| 5,486,292 A | 1/1996 | Bair et al. |
| 5,547,607 A | 8/1996 | Ando et al. |
| 5,562,824 A | 10/1996 | Magnusson |
| 5,611,832 A | 3/1997 | Suzuki et al. |
| 5,744,236 A | 4/1998 | Rohrbach et al. |
| 5,759,394 A | 6/1998 | Rohrbach et al. |
| 5,798,220 A | 8/1998 | Kossovsky |
| 5,800,706 A | 9/1998 | Fischer |
| 5,804,295 A | 9/1998 | Braun et al. |
| 5,855,788 A | 1/1999 | Everhart et al. |
| 5,865,968 A | 2/1999 | Denton et al. |
| 6,010,606 A | 1/2000 | Denton et al. |
| 6,057,488 A | 5/2000 | Koper et al. |
| 6,077,588 A | 6/2000 | Koslow et al. |
| 6,155,432 A | 12/2000 | Wilson et al. |
| 6,197,515 B1 | 3/2001 | Bamdad et al. |
| 6,200,482 B1 | 3/2001 | Winchester et al. |
| 6,235,388 B1 | 5/2001 | Yamamoto et al. |
| 6,290,848 B1 | 9/2001 | Tanner et al. |
| 6,321,915 B1 | 11/2001 | Wilson et al. |
| 6,344,071 B1 | 2/2002 | Smith et al. |
| 6,355,330 B1 | 3/2002 | Koslow et al. |
| 6,402,819 B1 | 6/2002 | De Ruiter et al. |
| 6,420,293 B1 | 7/2002 | Chang et al. |
| 6,464,757 B2 | 10/2002 | Zhang et al. |
| 6,514,413 B2 | 2/2003 | Pimenov et al. |
| 6,524,477 B1 | 2/2003 | Hughes |
| 6,550,622 B2 | 4/2003 | Koslow |
| 6,565,749 B1 | 5/2003 | Hou et al. |
| 6,630,016 B2 | 10/2003 | Koslow |
| 6,660,172 B2 | 12/2003 | Koslow |
| 6,716,218 B2 | 4/2004 | Holmes et al. |
| 6,716,525 B1 | 4/2004 | Yadav et al. |
| 6,797,167 B2 | 9/2004 | Koslow |
| 6,830,822 B2 | 12/2004 | Yadav |
| 7,842,762 B2 * | 11/2010 | Zawacky ............ C09D 5/4496 204/471 |
| 2009/0042060 A1 | 2/2009 | Zawacky et al. |
| 2011/0224328 A1 | 9/2011 | McCollum et al. |
| 2012/0220770 A1 | 8/2012 | Hickenboth et al. |

OTHER PUBLICATIONS

Gelbard, Georges et al., "Polynitrogen Strong Bases: 1-New Syntheses of Biguanides and their Catalytic Properties in Transesterification Reactions", Tetrahedron Letters; Apr. 30, 1998; pp. 2743-2746, vol. 39, No. 18, Pergamon.

Bocharov, B. V., "Progress in the Chemistry of the Carbodiimides", (Russian Chemical Reviews, 1965, 34(3), pp. 212-219.

* cited by examiner

US 9,994,720 B2

METHODS FOR PRODUCING 1,5,7-TRIAZABICYCLO[4.4.0]DEC-5-ENE BY REACTION OF A DISUBSTITUTED CARBODIIMIDE AND DIPROPYLENE TRIAMINE

CROSS REFERENCE TO RELATED APPLICATION

This application is a divisional application of U.S. patent application Ser. No. 13/455,651, filed on Apr. 25, 2012, which is hereby incorporated by reference.

FIELD OF THE INVENTION

The present invention relates to methods for producing 1,5,7-triazabicyclo[4.4.0]dec-5-ene.

BACKGROUND OF THE INVENTION

It is known that bicyclic guanidines, such as 1,5,7-triazabicyclo[4.4.0]dec-5-ene (TBD), are chemically active and can be used to catalyze a variety of chemical reactions. An important consideration in the commercial exploitation of bicyclic guanidines as a catalyst (for any reaction) is that bicyclic guanidines be relatively inexpensive to purchase and/or easy to produce.

Published methods for synthesizing bicyclic guanidines, however, are often complicated, such as by using a multiple step and/or time consuming synthesis process. Others use prohibitively expensive and/or hazardous starting materials. Further, many published methods do not produce high yields of the desired products, or produce byproducts, such as aniline, that are difficult to separate from the bicyclic guanidines and may themselves be hazardous. Also, many of these methods produce bicyclic guanidines of different types that may be difficult to separate from one another, and/or produce bicyclic guanidines in forms that are difficult to handle.

There is therefore a need for safe and efficient methods for producing bicyclic guanidines.

SUMMARY OF THE INVENTION

The present invention is directed to a method for producing 1,5,7-triazabicyclo[4.4.0]dec-5-ene comprising forming a mixture comprising a disubstituted carbodiimide, dipropylene triamine and an ethereal solvent and/or an alcohol; and heating the mixture to cause the disubstituted carbodiimide to react with the dipropylene triamine.

The present invention is further directed to methods for producing 1,5,7-triazabicyclo[4.4.0]dec-5-ene comprising forming a mixture comprising a disubstituted carbodiimide and dipropylene triamine; and heating the mixture to cause the disubstituted carbodiimide to react with the dipropylene triamine.

DETAILED DESCRIPTION OF THE INVENTION

The present invention is directed to methods for producing bicyclic guanidines. More specifically, the present invention is directed to methods for producing 1,5,7-triazabicyclo[4.4.0]dec-5-ene comprising reacting a disubstituted carbodiimide with dipropylene triamine ("DPTA"), also known as bis(3-aminopropyl)amine.

As used herein, the term "disubstituted carbodiimides" refers to a compound having the formula $RN=C=NR^1$, wherein R and $R^1$ independently comprise an alkyl group, an aryl group or mixtures thereof. R and $R^1$ can be the same or different. In certain embodiments, the disubstituted carbodiimide comprises a dialkyl carbodiimide and the $R/R^1$ group is an aliphatic and/or cycloaliphatic alkyl group, for example, having 1 to 10 carbons; particularly suitable dialkylcarbodiimides include, without limitation, N,N'-diisopropylcarbodiimide (DIC) (i.e. when $R/R^1$ is an isopropyl group), N,N'-dicyclohexylcarbodiimide (DCC) (i.e. when $R/R^1$ is a cyclohexyl group), N,N'-di-tert-butylcarbodiimide (wherein $R/R^1$ is a tert-butyl group), and any combinations thereof.

In certain embodiments, the disubstituted carbodiimide comprises a diaryl carbodiimide and the $R/R^1$ group is an aryl group. A particularly suitable diarylcarbodiimide is N,N'-di-p-tolylcarbodiimide (wherein $R/R^1$ is a toluene residue). In certain embodiments, combinations of one or more dialkylcarbodiimides and/or one or more diarylcarbodiimides are used.

In certain embodiments, the method for producing 1,5,7-triazabicyclo[4.4.0]dec-5-ene includes first dissolving the disubstituted carbodiimide in an ethereal solvent and/or in an alcohol prior to reacting the disubstituted carbodiimide with DPTA. These embodiments are sometimes referred to herein as the "solvent process". In alternative embodiments discussed further below, methods for producing 1,5,7-triazabicyclo[4.4.0]dec-5-ene do not utilize an ethereal solvent or alcohol, and are sometimes referred to herein as the "solventless process".

In general, the solvent process begins by dissolving a disubstituted carbodiimide in an ethereal solvent and/or in an alcohol. Next, dipropylene triamine is added to the dissolved disubstituted carbodiimide. In some embodiments, the disubstituted carbodiimide and solvent and/or alcohol mixture is heated, such as to a temperature of 60° C., prior to the addition of the DPTA and in some embodiments the mixture is heated to about 60° C. after addition of the DPTA. The mixture is then further heated to an elevated temperature and held for a sufficient period of time to react the disubstituted carbodiimide and dipropylene triamine, first forming an intermediate, (generally an N,N'-disubstituted monocyclic guanidine), and then forming 1,5,7-triazabicyclo[4.4.0]dec-5-ene and an amine. The amine generated by the reaction of the disubstituted carbodiimide and dipropylene triamine depends on the $R/R^1$ group. For example, the amine will be isopropyl amine if $R/R^1$ is an isopropyl group, or cyclohexylamine, if $R/R^1$ is a cyclohexyl group. This amine byproduct can be distilled off during the course of the reaction, such that all that remains in the reaction vessel with the 1,5,7-triazabicyclo[4.4.0]dec-5-ene upon completion of the reaction is the ethereal solvent and/or the alcohol. Alternatively, the amine byproduct can be removed upon completion of the reaction.

Suitable ethereal solvents that may be utilized in the solvent process of the present invention include, but are not limited to, butyl carbitol formal.

Suitable alcohols (i.e. alcoholic solvents) that may be utilized in the solvent process of the present invention include, but are not limited to monoalcohols or polyols, such as 2-butoxyethanol (i.e. butyl cellosolve), diethylene glycol monobutyl ether (i.e. butyl CARBITOL), hexaethoxylated bisphenol A polyol and combinations thereof. In certain embodiments, 2-butoxyethanol is used.

In general, the solventless process of the present invention begins by introducing the disubstituted carbodiimide to a reaction vessel. Next, dipropylene triamine is slowly added to reaction vessel, wherein the resultant mixture begins to react and exotherm. The mixture is then heated to an elevated temperature and held for a sufficient period of time to react the disubstituted carbodiimide and dipropylene triamine, first forming an intermediate and then forming 1,5,7-triazabicyclo[4.4.0]dec-5-ene and an amine. This amine byproduct can be distilled off during the course of the reaction, or removed upon completion of the reaction. A diluent, such as hexaethoxylated bisphenol A polyol, may be added to the formed 1,5,7-triazabicyclo[4.4.0]dec-5-ene in the reaction vessel.

The term "an elevated temperature", when used in the context of the present processes is the temperature at which the disubstituted carbodiimide reacts with the dipropylene triamine to form the 1,5,7-triazabicyclo[4.4.0]dec-5-ene and the amine. In certain embodiments, the elevated temperature is 160° C. or greater, 170° C. or greater, or 180° C. or greater, and can be as high as 220° C., 230° C., 240° C. or even higher. Typically, a higher temperature results in shorter reaction time. In certain solvent processes, the elevated temperature corresponds to the reflux temperature of the ethereal solvent and/or the alcohol or blend that is used. For example, when 2-butoxyethanol is used, the elevated temperature corresponds to the reflux temperature of 2-butoxyethanol (about 170° C.). In a particular embodiment, the disubstituted carbodiimide comprises diaryl carbodiimide and the elevated temperature is 160° C. or greater, 170° C. or greater or 180° C. or greater.

The term "a sufficient period of time", when used in the context of the present process, is the time needed to cause the disubstituted carbodiimide to substantially or completely react with dipropylene triamine. By "substantially react" is meant 70% conversion or greater; by "completely react" is meant 85% conversion or greater. This time period may vary, depending upon the exact reaction conditions and, in the case of the solvent process, depending upon the ethereal solvent and/or the alcohol used. Typically, the sufficient period of time will be 1 to 6 hours, such as 1 to 4 hours or 2 to 4 hours. The degree of reaction can be determined by analyzing the contents of the reaction vessel using known spectroscopic techniques (IR, $^{13}$C NMR, etc.) to confirm the presence or absence of the disubstituted carbodiimide and dipropylene triamine and to confirm the presence of 1,5,7-triazabicyclo[4.4.0]dec-5-ene.

In certain embodiments, the processes described herein are performed without catalyst.

In certain embodiments, the 1,5,7-triazabicyclo[4.4.0] dec-5-ene is isolated from the ethereal solvent and/or the alcohol through distillation at atmospheric pressure. In certain embodiments, after the distillation process, the 1,5,7-triazabicyclo[4.4.0]dec-5-ene may be recovered in powder form. Alternatively, the 1,5,7-triazabicyclo[4.4.0]dec-5-ene may be maintained in solution with the ethereal solvent and/or with the alcohol for subsequent use. As noted above, in both the solvent and solventless processes the amine byproduct can be removed from the reaction vessel via distillation. In certain embodiments, this distillation is performed concurrent with the reaction. By "concurrent" is meant the distillation is performed during the reaction in which the 1,5,7-triazabicyclo[4.4.0]dec-5-ene is formed. Although the inventors do not wish to be bound by any mechanism, in certain embodiments, distilling off the amine byproduct concurrently with the reaction may result in the reaction occurring more efficiently, that is, more quickly and/or with a higher percent conversion.

The isolated bicyclic guanidine (1,5,7-triazabicyclo [4.4.0]dec-5-ene (TBD)), formed in either the solvent or solventless processes described above, which is in solution form or powder form, can then be added to any composition in which bicyclic guanidine can be used. For example, in certain embodiments, the bicyclic guanidine formed from the process described herein can be added to an electrodepositable coating composition, such as the electrodepositable coating composition that is described in U.S. Pat. No. 7,842,762, which is incorporated in its entirety herein by reference.

As used herein, unless otherwise expressly specified, all numbers such as those expressing values, ranges, amounts or percentages may be read as if prefaced by the word "about", even if the term does not expressly appear. Any numerical range recited herein is intended to include all sub-ranges subsumed therein. Plural encompasses singular and vice versa. For example, while the invention has been described in terms of "a" disubstituted carbodiimide, "an" alcohol, "the" R/R$^1$ group, and the like, mixtures of these and other components can be used. Also, as used herein, the term "polymer" is meant to refer to prepolymers, oligomers and both homopolymers and copolymers; the prefix "poly" refers to two or more. When ranges are given, any endpoints of those ranges and/or numbers within those ranges can be combined with the scope of the present invention. "Including", "such as", "for example" and like terms means "including/such as/for example but not limited to".

EXAMPLES

The following examples are intended to exemplify the invention and are not intended to limit the invention in any way.

Example 1: DIC Route in 2-butoxyethanol

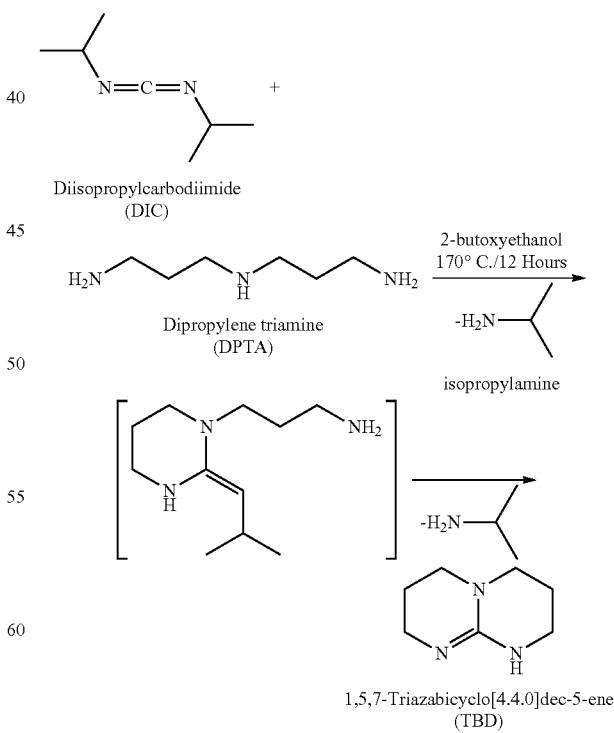

A 4-neck flask was equipped with a temperature probe, stainless steel mechanical stirrer, and an ice water condenser.

Dry nitrogen was swept through the flask, out through the condenser, then through an attached cold trap containing dry ice and ethanol used to trap isopropylamine distillate. The flask was charged with 2-butoxyethanol (220 mL) and N,N'-diisopropylcarbodiimide (151.4 g, 1.2 mol), and warmed to 60° C. Then, dipropylene triamine (131.2 g, 1.0 mol) was added slowly. Upon addition of dipropylene triamine, an exotherm of 40° C. was observed (~60° C.→100° C.). The reaction was warmed slowly to 170° C. and refluxed at that temperature for 12 hours. The orange, homogenous solution was then cooled, poured out of the reaction vessel, and used without further purification. The concentration of TBD in the final solution was determined by HPLC (38.8 wt %, 94.6% conversion). $^{13}$C NMR analysis indicated that the material consisted solely of 1,5,7-triazabicyclo[4.4.0]dec-5-ene in 2-butoxyethanol. $^{13}$C NMR analysis of the distillate confirmed the capture of the byproduct isopropylamine (129 mL) as the sole compound.

Example 2: DCC Route in 2-butoxyethanol

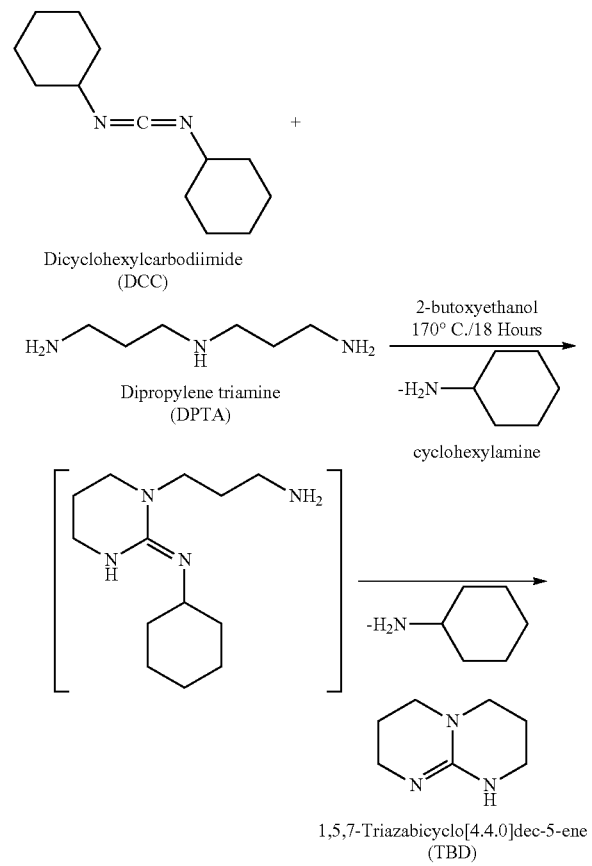

A 4-neck flask was equipped with a temperature probe, stainless steel mechanical stirrer, and an ice water condenser. Dry nitrogen was swept through the flask and out through the condenser. The flask was charged with 2-butoxyethanol (220 mL) and N,N'-dicyclohexylcarbodiimide (247.6 g, 1.2 mol), and warmed to 60° C. Then, dipropylene triamine (131.2 g, 1.0 mol) was added slowly. Upon addition of dipropylene triamine, an exotherm of 14° C. was observed (~58° C.→72° C.). The reaction was warmed slowly to 170° C. and refluxed at that temperature for 18 hours. The orange, homogenous solution was then cooled, poured out of the reaction vessel, and used without further purification. The concentration of TBD in the final solution was determined by HPLC (32.9 wt %, 80.2% conversion). $^{13}$C NMR analysis indicated that the material consisted of 1,5,7-triazabicyclo[4.4.0]dec-5-ene and cyclohexylamine (2.5%) in 2-butoxyethanol.

Example 3: DCC Route in Diethylene Glycol Monobutyl Ether

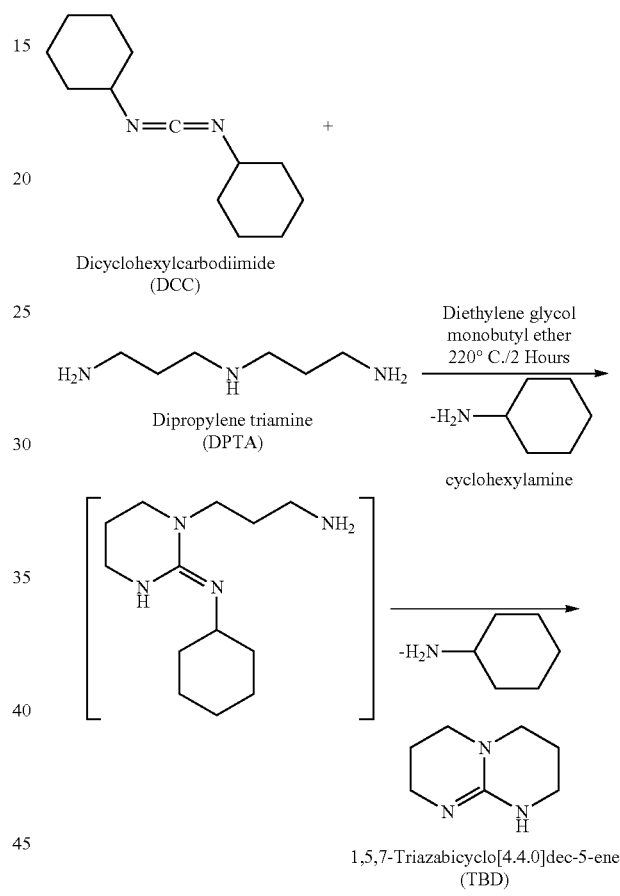

A 4-neck flask was equipped for total distillation, along with a temperature probe and stainless steel mechanical stirrer. Dry nitrogen was swept through the flask and out through the distillation apparatus. The flask was charged with diethylene glycol monobutyl ether (210 mL) and N,N'-dicyclohexylcarbodiimide (247.6 g, 1.2 mol), and warmed to 60° C. Then, dipropylene triamine (131.2 g, 1.0 mol) was added slowly. Upon addition of dipropylene triamine, an exotherm of 41° C. was observed (~61° C.→102° C.). The reaction was warmed to 140° C. and held for 1 hour, then heated to 220° C. and held for 2 hours. The orange, homogenous solution was then cooled, poured out of the reaction vessel, and used without further purification. The concentration of TBD in the final solution was determined by HPLC (35.4 wt %, 81.0% conversion). $^{13}$C NMR analysis indicated that the material consisted solely of 1,5,7-triazabicyclo[4.4.0]dec-5-ene in diethylene glycol monobutyl ether. $^{13}$C NMR and GC/MS analysis of the distillate confirmed the capture of cyclohexylamine (199 mL).

Example 4: DpTC Route in 2-butoxyethanol

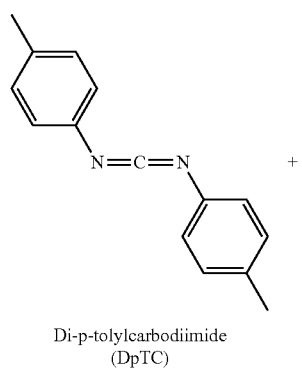

Di-p-tolylcarbodiimide
(DpTC)

+

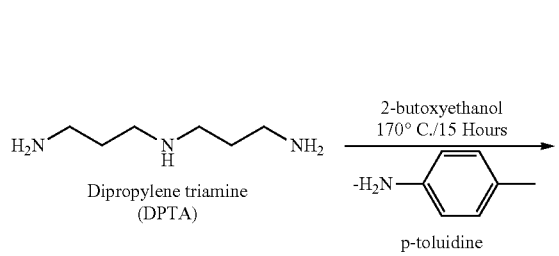

Dipropylene triamine
(DPTA)

2-butoxyethanol
170° C./15 Hours
$\longrightarrow$
-H$_2$N-⬡-CH$_3$
p-toluidine

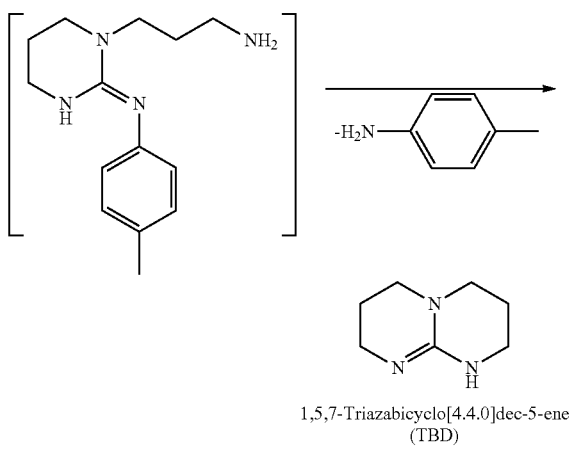

1,5,7-Triazabicyclo[4.4.0]dec-5-ene
(TBD)

A 4-neck flask was equipped with a temperature probe, magnetic stir bar, and an ice water condenser. Dry nitrogen was swept through the flask and out through the condenser. The flask was charged, at ambient temperature, with 2-butoxyethanol (11 mL), N,N'-di-p-tolylcarbodiimide (13.5 g, 0.06 mmol), and dipropylene triamine (6.64 g, 0.05 mol). An exotherm of 34° C. was observed (~23° C.→57° C.). The reaction was warmed slowly to 170° C. and refluxed at that temperature for 15 hours. The orange-brown, homogenous solution was then cooled, poured out of the reaction vessel, and used without further purification. The concentration of TBD in the final solution was determined by HPLC (19.9 wt %, 79.1% conversion). $^{13}$C NMR and GC analyses indicated that the material consisted of 1,5,7-triazabicyclo[4.4.0]dec-5-ene and p-toluidine (36.8%) in 2-butoxyethanol.

Example 5: DCC Route (100% Solids, Polyol Post-add, 20% DCC Excess)

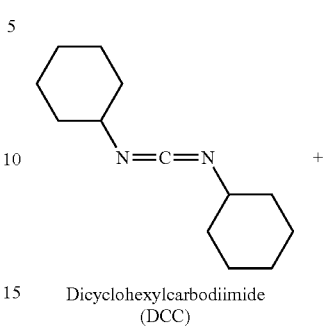

Dicyclohexylcarbodiimide
(DCC)

+

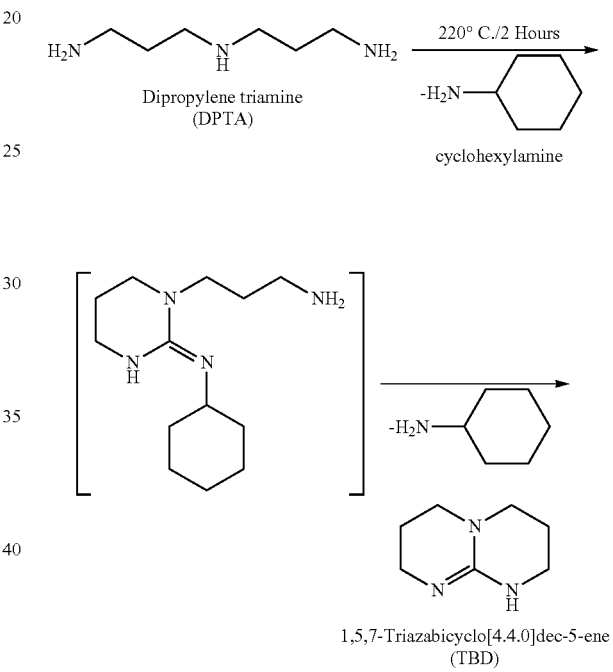

A 4-neck flask was equipped for total distillation, along with a temperature probe and stainless steel mechanical stirrer. Dry nitrogen was swept through the flask and out through the distillation apparatus. The flask was charged with N,N'-dicyclohexylcarbodiimide (247.6 g, 1.2 mol) followed by the slow addition of dipropylene triamine (131.2 g, 1.0 mol). Upon addition of dipropylene triamine, an exotherm of 31° C. was observed (~24° C.→55° C.). The reaction was warmed to 170° C. and held for 1 hour, then heated to 220° C. and held for 2 hours. After the final hold, hexaethoxylated bisphenol A polyol (417.0 g, 0.85 mol) was added as a diluent. The orange, homogenous solution was then stirred, cooled, poured out of the reaction vessel, and used without further purification. The concentration of TBD in the final solution was determined by HPLC (21.3 wt %, 94.4% conversion). $^{13}$C NMR analysis indicated that the material consisted solely of 1,5,7-triazabicyclo[4.4.0]dec-5-ene in hexaethoxylated bisphenol A polyol. $^{13}$C NMR and GC/MS analysis of the distillate confirmed the capture of cyclohexylamine (175 mL).

Example 6: DCC Route (100% Solids, Polyol Post-add, 2% DCC Excess)

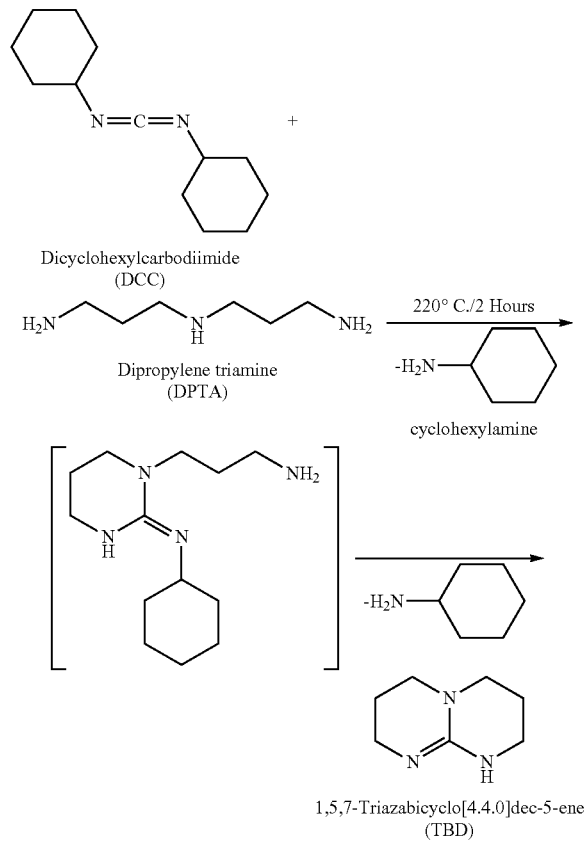

A 4-neck flask was equipped for total distillation, along with a temperature probe and stainless steel mechanical stirrer. Dry nitrogen was swept through the flask and out through the distillation apparatus. The flask was charged with N,N'-dicyclohexylcarbodiimide (210.5 g, 1.02 mol) followed by the slow addition of dipropylene triamine (131.2 g, 1.00 mol). Upon addition of dipropylene triamine, an exotherm of 32° C. was observed (~23° C.→55° C.). The reaction was warmed to 170° C. and held for 1 hour, then heated to 220° C. and held for 2 hours. After the final hold, hexaethoxylated bisphenol A polyol (319.8 g, 0.65 mol) was added as a diluent. The orange, homogenous solution was then stirred, cooled, poured out of the reaction vessel, and used without further purification. The concentration of TBD in the final solution was determined by HPLC (28.0 wt %, 93.7% conversion). $^{13}$C NMR analysis indicated that the material consisted solely of 1,5,7-triazabicyclo[4.4.0]dec-5-ene in hexaethoxylated bisphenol A polyol. $^{13}$C NMR and GC/MS analysis of the distillate confirmed the capture of cyclohexylamine (229 mL).

Whereas particular embodiments of this invention have been described above for purposes of illustration, it will be evident to those skilled in the art that numerous variations of the details of the present invention may be made without departing from the invention as defined in the appended claims.

What is claimed is:

1. An electrodepositable coating composition comprising (a) 1,5,7-triazabicyclo[4.4.0]dec-5-ene and an epoxy functional polymer that react to form a reaction product, and (b) an amine byproduct, wherein the 1,5,7-triazabicyclo[4.4.0]dec-5-ene and the amine byproduct are formed by heating a mixture comprising a disubstituted carbodiimide, dipropylene triamine and an ethereal solvent and/or an alcohol at a temperature of at least 160° C. to cause the disubstituted carbodiimide to react with the dipropylene triamine, and the amine byproduct comprises cyclohexylamine, isopropyl amine, p-toluidine, tert-butylamine, or combinations thereof.

2. The electrodepositable coating composition of claim 1, wherein the disubstituted carbodiimide comprises dialkylcarbodiimide.

3. The electrodepositable coating composition of claim 1, wherein the disubstituted carbodiimide comprises diarylcarbodiimide.

4. The electrodepositable coating composition of claim 1, wherein the amine byproduct is reactive with the epoxy functional polymer to form a second reaction product.

5. The electrodepositable coating composition of claim 1, further comprising a curing agent.

6. A coated substrate formed by electrophoretically applying and curing the electrodepositable coating composition of claim 1 onto at least a portion of a substrate.

7. An electrodepositable coating composition comprising (a) 1,5,7-triazabicyclo[4.4.0]dec-5-ene and an epoxy functional polymer that react to form a reaction product, and (b) an amine byproduct, wherein the 1,5,7-triazabicyclo[4.4.0]dec-5-ene and the amine byproduct are formed by heating a mixture comprising a disubstituted carbodiimide and dipropylene triamine at a temperature of at least 160° C. to cause the disubstituted carbodiimide to react with the dipropylene triamine, and the amine byproduct comprises cyclohexylamine, isopropyl amine, p-toluidine, tert-butylamine, or combinations thereof.

8. The electrodepositable coating composition of claim 7, further comprising a diluent added to the mixture after formation of the 1,5,7-triazabicyclo[4.4.0]dec-5-ene.

9. The electrodepositable coating composition of claim 7, wherein the disubstituted carbodiimide comprises dialkylcarbodiimide.

10. The electrodepositable coating composition of claim 7, wherein the disubstituted carbodiimide comprises diarylcarbodiimide.

11. The electrodepositable coating composition of claim 7, wherein the amine byproduct is reactive with the epoxy functional polymer to form a second reaction product.

12. The electrodepositable coating composition of claim 7, further comprising a curing agent.

13. A coated substrate formed by electrophoretically applying and curing the electrodepositable coating composition of claim 7 onto at least a portion of a substrate.

* * * * *